United States Patent
van Hoogevest

(10) Patent No.: US 6,683,100 B2
(45) Date of Patent: *Jan. 27, 2004

(54) ORGANIC COMPOUNDS

(75) Inventor: Peter van Hoogevest, Bubendorf (CH)

(73) Assignee: Novartis AG, Basel (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 172 days.

(21) Appl. No.: 09/233,408

(22) Filed: Jan. 19, 1999

(65) Prior Publication Data

US 2002/0115686 A1 Aug. 22, 2002

(51) Int. Cl.$^7$ .................. A61K 31/425; A61K 31/35
(52) U.S. Cl. ............................ 514/365; 514/456
(58) Field of Search ................. 514/456, 365

(56) References Cited

U.S. PATENT DOCUMENTS

| | | | |
|---|---|---|---|
| 3,459,731 A | 8/1969 | Gramera et al. | 260/209 |
| 4,383,992 A | 5/1983 | Lipari | 424/238 |
| 4,535,152 A | 8/1985 | Szejtli et al. | 536/103 |
| 4,659,696 A | 4/1987 | Hirai et al. | 514/15 |
| 5,496,804 A | 3/1996 | Reed et al. | 514/12 |
| 5,565,478 A | 10/1996 | Kohn et al. | 514/359 |
| 5,641,803 A | 6/1997 | Carretta et al. | 514/449 |
| 5,977,163 A * | 11/1999 | Li et al. | 514/449 |

FOREIGN PATENT DOCUMENTS

| | | |
|---|---|---|
| CA | 1222697 | 6/1987 |
| DE | 31 182 18 | 4/1982 |
| DE | 33 170 64 | 11/1984 |
| DE | 33 461 23 | 6/1985 |
| DE | 41 38 042 | 5/1993 |
| DE | 42 07 922 | 9/1993 |
| EP | 0 094 157 | 11/1983 |
| EP | 0 149 197 | 7/1985 |
| EP | 0 197 571 | 10/1986 |
| EP | 0 091 781 | 11/1986 |
| EP | 0 292 050 | 11/1988 |
| EP | 300 526 | 1/1989 |
| EP | 0 320 032 | 6/1989 |
| EP | 0 396 184 | 11/1990 |
| EP | 0 499 322 | 8/1992 |
| EP | 0 503 710 | 9/1992 |
| EP | 0 636 634 | 2/1995 |
| EP | 0 818 469 | 1/1998 |
| GB | 2189245 | 10/1987 |
| WO | WO 90/12035 | 10/1990 |
| WO | WO 91/07967 | 6/1991 |
| WO | WO 91/11200 | 8/1991 |
| WO | WO 93/10121 | 5/1993 |
| WO | WO 93/19061 | 9/1993 |
| WO | WO 93/23017 | 11/1993 |
| WO | WO 94/26728 | 11/1994 |
| WO | WO 95/08993 | 4/1995 |
| WO | WO 95/31178 | 11/1995 |
| WO | WO 96/14090 | 5/1996 |
| WO | WO 97/18839 | 5/1997 |
| WO | WO 97/19086 | 5/1997 |
| WO | WO 97/33552 | 9/1997 |
| WO | WO 98/08849 | 3/1998 |
| WO | WO 98/22461 | 5/1998 |
| WO | WO 98/25929 | 6/1998 |
| WO | WO 98/38192 | 9/1998 |
| WO | WO 99/01124 | 1/1999 |
| WO | WO 99/02514 | 1/1999 |
| WO | WO 99/07692 | 2/1999 |

OTHER PUBLICATIONS

Bollag, Expert Opin. Invest. Drugs, 6(7), pp 867–873 Abstract Only, 1997.*

Akiyama et al., Somatic Cell and Molecular Genetics, vol. 11 (2), "Isolation and Genetic Characterization of Human KB Cell Lines Resistant to Multiple Drugs," pp. 117–126 (1985).

Balog A. et al., Angew. Chem. Int. Ed. Engl., vol. 35 (23/24), "Total Synthesis of (–)–Epothilone A," pp. 2801–2803 (1996).

Balog A. et al., Tetrahedron Letters, vol. 38 (26), "Stereoselective Syntheses and Evaluation of Compounds in the 8–Desmethylepothilone A Series: Some Suprising Observations Regarding Their Chemical and Biological Properties," pp. 4529–4532 (1997).

Bertinato P. et al., J. Org. Chem., vol. 61, "Studies toward a Synthesis of Epothilone A: Stereo–controlled Assembly of the Acyl Region and Models for Macrocyclization," pp. 8000–8001 (1996).

Blagoskonny et al., Cancer Research, vol. 57, "Raf–1/bcl–2 Phosphorylation: A Step from Microtubule Damage to Cell Death," pp. 130–135 (1997).

Blechert S. and Dollt H., Liebigs Ann., "Synthesis of (–)–Streptenol A, (±)–Streptenol B, C and D," pp. 2135–2140 (1996).

Bollag D. et al., Cancer Research, vol. 55, "Epothilones, a New Class of Microtubule–stabilizing Agents with a Taxol–like Mechanism of Action," pp. 2325–2333 (1995).

Bollag D.M., Exp. Opin. Invest. Drugs, vol. 6 (7), "Epothilones: novel microtubule–stabilising agents," pp. 867–873 (1997).

Chemical Abstracts 98:124208s, Koho, JP 57,194,787 Nov. 30, 1982.

(List continued on next page.)

Primary Examiner—Jerome D. Goldberg
(74) Attorney, Agent, or Firm—George R. Dohmann

(57) ABSTRACT

Pharmaceutical formulations comprising an epothilone in the form of an infusion concentrate or a lyophilised composition, and methods of administration of an epothilone in suitable form for parenteral administration.

20 Claims, No Drawings

OTHER PUBLICATIONS

Chemical Abstracts 96:223270w, Koho, JP 82 24,312 Feb. 8, 1982.

Chou et al., PNAS USA, vol. 95, "Desoxyepothilone B: An efficacious microtubule–targeted antitumor agent with a promising in vivo profile relative to epothilone B," pp. 9642–9647 (1998).

Chou et al., Proceedings of the American Association for Cancer Research, New Orleans, Mar. 28–31, 1998, vol. 39, "Pharmacologic comparison of epothilones and taxol," pp. 163–164, Abstract #1119 (1998).

Claus E. et al., Tetrahedron Letters, vol. 38 (8), "Synthesis of the C1–C9 Segment of Epothilons," pp. 1359–1362 (1997).

Finlay R. Chemistry & Industry, "Metathesis vs. metastasis: the chemistry and biology of the epothilones," pp. 991–996 (Dec. 15, 1997).

Fojo et al., Cancer Research, vol. 45, "Reduced Drug Accumulation in Multiply Drug–resistant Human KB Carcinoma Cell Lines," pp. 3002–3007 (1985).

Gabriel T. and Wessjohann L., Tetrahedron Letters, vol. 38 (8), "The Chromium–Reformatsky Reaction: Asymmetric Synthesis of the Aldol Fragment of the Cytotoxic Epothilons from 3–(–2–Bromoacyl)–2–oxazolidinones," pp. 1363–1366 (1997).

Gerth K. et al., The Journal of Antibiotics, vol. 49 (6), "Epothilons A and B: Antifungal and Cytotoxic Compounds from *Sorangium cellulosum* (Myxobacteria)—Production, Physico–chemical and Biological Properties," pp. 560–563 (1996).

Giannakakou et al., The Journal of Biological Chemistry, vol. 27, "Paclitaxel–resistant Human Ovarian Cancer Cells Have Mutant β–Tubulins That Exhibit Impaired Paclitaxel–driven Polymerization," pp. 17118–17125 (1997).

Grever et al., Seminars in Oncology, vol. 19 (6), "The National Cancer Institute: Cancer Drug Discovery and Development Program," pp. 622–638 (1992).

Grubbs R. et al., Acc. Chem. Res., vol. 28, "Ring–Closing Metathesis and Related Processes in Organic Synthesis," pp. 446–452 (1995).

Höfle G. et al., Angew. Chem., vol. 108 (13/14), "Epothilon A and B—neuartige, 16gliedrige Makrolide mit cytotoxischer Wirkung: Isolierung, Struktur im Kristall und Konformation in Lösung," pp. 1671–1673 (1996) In German, with partial English translation.

Höfle G. et al., Angew. Chem. Int. Ed. Engl., vol. 35 (13/14), "Epothilone A and B—Novel 16–Membered Macrolides with Cytotoxic Activity: Isolation, Crystal Structure, and Conformation in Solution," pp. 1567–1569 (1996).

Horikoshi K., Chemical Economy & Engineering Review, vol. 13 (1–2), "Alkalophilic Microorganisms and New Fermentation Technique—Industrial Production of Cyclodextrin," pp. 7–11 (1981).

Jordan et al., Med. Res. Rev., vol. 18,"Tubulin as a Target for Anticancer Drugs: Agents Which Interact with the Mitotic Spindle," pp. 259–295 (1998).

Kang Y. et al., Chem. Commun., "Stable bis(silyl)nickel complexes with o–carboranyl unit: a facile double silylation of alkynes and alkenes," pp. 2343–2344 (1998).

Keller–Schierlein W. et al., Helv. Chem. Acta, vol. 66 (4), "Metabolites of microorganisms," pp. 1253–1261 (1983) (with English Abstract).

Kowalski et al., J. Biol. Chem., vol. 272 (4), "Activities of the Microtubule–stabilizing Agents Epothilones A and B with Purified Tubulin and in Cells Resistant to Paclitaxel (Taxol®)," pp. 2534–2541 (1997).

Loftsson T. and Brewster M., Journal of Pharmaceutical Sciences, vol. 85 (10), "Pharmaceutical Applications of Cyclodextrins. 1. Drug Solubilization and Stabilization," pp. 1017–1025 (1996).

May S. and Grieco P., Chem. Commun., "Total synthesis of (–)–epothilone B," pp. 1597–1598 (1998).

Meng D. et al., J. Org. Chem., vol. 61, "Studies toward a Synthesis of Epothilone A: Use of Hydropyran Templates for the Management of Acyclic Stereochemical Relationships," pp. 7998–7999 (1996).

Meng D. et al., J. Am. Chem. Soc., vol. 119, "Total Syntheses of Epothilones A and B," pp. 10073–10092 (1997).

Meng D. et al., J. Am. Chem. Soc., vol. 119, "Remote Effects in Macrolide Formation through Ring–Forming Olefin Metathesis: An Application to the Synthesis of Fully Active Epothilone Congeners," pp. 2733–2734 (1997).

Meyer et al., Int. J. Cancer, vol. 43, "A Derivative of Staurosporine (CGP 41 251) Shows Selectively for Protein Kinase C Inhibition and In Vitro Anti–Proliferative as well as In Vivo Anti–Tumor Activity," pp. 851–856 (1989).

Meyers A. et al., J. Org. Chem., vol. 38 (12), "1,4 Addition of Organometallics to 2–Alkenyldihydro–1,3–oxazines. A Synthesis of α–Substituted Aldehydes and Ketones," pp. 2136–2143 (1973).

Moasser et al., PNAS USA, vol. 95, "Farnesyl transferase inhibitors cause enhanced mitotic sensitivity to taxol and epothilones," pp. 1369–1374 (1998).

Mühlradt et al., Cancer Research, vol. 57, "Epothilone B Stabilizes Microtubuli of Macrophages Like Taxol without Showing Taxol–like Endotoxin Activity," pp. 3344–3346 (1997).

Mulzer J. and Mantoulidis A., Tetrahedron Letters, vol. 37 (51), "Synthesis of the C(1)–C(9) Segment of the Cytotoxic Macrolides Epothilon A and B," pp. 9179–9182 (1996).

Nerdel F. et al., Chem. Ber., vol. 100 (3), "Fragmentation reactions of carbonyl compounds with electro–negative substituents in the β–position. IV. 6–Heptenoic acids and bicyclo[3.1.1]– and –[3.2.0]heptan–6–one," pp. 720–735 (1967) (with English Abstract).

Nicolaou K.C. et al., Angew. Chem. Int. Ed. Engl., vol. 35 (20), "An Approach to Epothilones Based on Olefin Metathesis," pp. 2399–2401 (1996).

Nicolaou K.C. et al., Nature, vol. 387, "Synthesis of epothilones A and B in solid and solution phase," pp. 268–272 (1997).

Nicolaou K.C. et al., J. Am. Chem. Soc., vol. 119, "Total Syntheses of Epothilones A and B via a Macrolactonization–Based Strategy," pp. 7974–7991 (1997).

Nicolaou et al., Angew. Chem. Int. Ed., vol. 36 (19), "Designed Epothilones: Combinatorial Synthesis, Tubulin Assembly Properties, and Cytotoxic Action against Taxol–Resistant Tumor Cells," pp. 2097–2103 (1997).

Nicolaou et al., Angew. Chem. Int. Ed., vol. 37, "Chemical Biology of Epothilones," pp. 2014–2045 (1998).

Nicolaou et al., Chemistry & Biology, vol. 5 (7), "Synthesis and biological properties of C12, 13–cyclopropyl–epothilone A and related epothilones," pp. 365–372 (1998).

Nicolaou K. et al., Journal of the American Chemical Society, vol. 119, "The Olefin Metathesis Approach to Epothilone A and Its Analogues," pp. 7960–7973 (1997).

Nicolaou K. et al., Chem. Commun., "Total synthesis of 26–hydroxyepothilone B and related analogues," pp. 2343–2344 (1997).

Nicolaou K. et al., Tetrahedron, vol. 54, "Total Synthesis of 26–Hydroxy–Epothilone B and Related Analogs via Macrolactonization Based Strategy," pp. 7127–7166 (1998).

Nicolaou K. et al., Angew. Int. Ed. Engl., vol. 33, "Chemistry and Biology of Taxol," pp. 15–44 (1994).

Nicolaou K. et al., Angew. Chem. Int. Ed. Engl., vol. 36 (5), "Total Synthesis of Epothilone A: The Macrolactonization Approach," pp. 525–527 (1997).

Rajewski R. and Stella V., Journal of Pharmaceutical Sciences, vol. 85 (11), "Pharmaceutical Applications of Cyclodextrins. 2. In Vivo Drug Delivery," pp. 1142–1169 (1996).

Rowinsky E., Annu. Rev. Med., vol. 48, "The Development and Clinical Utility of the Taxane Class of Antimicrotubule Chemotherapy Agents," pp. 353–374 (1997).

Schiff P. et al., Nature, vol. 277, "Promotion of microtubule assembly in vitro by taxol," pp. 665–667 (1979).

Schinzer D. et al., Angew. Chem. Int. Ed. Engl., vol. 36 (5), "Total Synthesis of (–)–Epothilone A," pp. 523–524 (1997).

Su Dai–Shi et al., Angew. Chem. Int. Ed. Engl., vol. 36 (19), "Structure–Activity Relationships of the Epothilones and the First In Vivo Comparison with Paclitaxel," pp. 2093–2096 (1997).

Taylor R. and Haley J., Tetrahedron Letters, vol. 38 (12), "Towards the Synthesis of Epothilone A: Enantioselective Preparation of the Thiazole Sidechain and Macrocyclic Ring Closure," pp. 2061–2064 (1997).

Wartmann et al., Proceedings of the American Association for Cancer Research, New Orleans, Mar. 28–31, 1998, vol. 39, "In vitro and in vivo activity profile of the microtubule–stabilizing agents epothilone A and B," Abstract #1118 (1998).

Winkler J. and Axelsen P., Bioorganic & Medicinal Chemistry Letters, vol. 6 (24), "A Model for the Taxol (Paclitaxel)/Epothilone Pharmacophore," pp. 2963–2966 (1996).

Wolff et al., Int. J. Oncol., vol. 11, "Epothilone A induces apoptosis in neuroblastoma cells with multiple mechanisms of drug resistance," pp. 123–126 (1997).

Yang Z. et al., Angew. Chem. Int. Ed. Engl., vol. 36 (1/2), "Total Synthesis of Epothilone A: The Olefin Metathesis Approach," pp. 166–168 (1997).

* cited by examiner

ORGANIC COMPOUNDS

This invention is concerned with formulations of epothilones, and in particular formulations which are administrable intravenously.

The epothilones represent a class of microtubule stabilizing cytotoxic agents (see Gerth, K. et al., J. Antibiot. 49, 560-3 (1966); or Hoefle et al., DE 41 38 042) of the formula I. Typical representatives include epothilone A wherein R is a hydrogen and epothilone B wherein R is a methyl group.

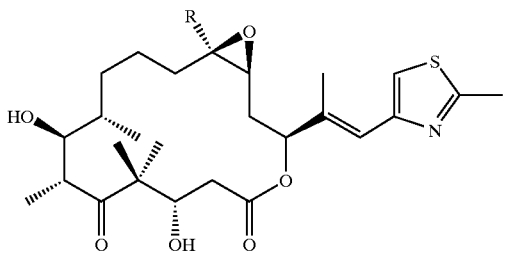

They are 16-member macrolides containing seven, chiral centers and may also be characterized by various functionalities. For example, they may include other ring systems, such as an epoxide and/or a thiazole ring. They may have two free, derivatizable hydroxyl groups and the macrolide itself may comprise an ester linkage. The epothilones and their syntheses are described for example in published PCT application number WO 93/10121 and DE 41 38 042 A2, the contents of which are incorporated herein by reference. Typical epothilone derivatives and their syntheses are described in published PCT application number WO 97/19086 and WO 98/25929, the contents of which are incorporated herein by reference. Reference to the epothilones is preferably intended to mean epothilone A or epothilone B or their salts and derivatives or mixtures thereof as appropriate. Epothilone A or B may be used alone or they may be used as mixtures of A and B, preferably however they are used as solely A or solely B, most preferably solely B.

Cytotoxic agents are well known for the treatment of tumours. The anti-tumour activity of many of these compounds relies on the inhibition of cell proliferation and consequent induction of apoptosis and cell death. The majority of cytotoxic agents exert their effects through interference of DNA and/or RNA syntheses. However, for certain cytotoxic agents, e.g. members of the taxane family, e.g. paclitaxel, and the epothilones, their activity is reliant on their interference with microtubule dynamics. Microtubules are an important and attractive target for development of novel anti-cancer formulations.

However, little has been published on formulations suitable for epothilones. We have found that the 16-member macrolide system is particularly labile to degradation. Moreover, the poor solubility of these compounds makes it very difficult to form formulations for parenteral administration. Poorly soluble compounds conventionally may be brought into solution by warming the solvent during the dissolution process. However, given the high reactivity of these compounds they may be prone to degradation at elevated temperatures. Further, these highly reactive compounds may degrade over prolonged periods of storage as aqueous solutions. Concentrated solutions of the microtubule agent Taxol® which can be diluted in an aqueous medium prior to intravenous administration have been described. However, such solutions conventionally employ a surfactant such as Cremophor® (polyethoxylated castor oil). It is well known that surfactants such as Cremophor® can cause allergic reactions in patients.

Thus there is a need for commercially acceptable formulations suitable for epothilones, e.g. formulations which allow for storage, e.g. in a refrigerator, e.g. at 2–8° C.

We have now surprisingly found means to improve the solubility of epothilone A and B and/or render them more rapidly soluble without the use of a surfactant, for example a surfactant having an HLB value of 10 or more, e.g. Cremophor®, and without adversely affecting their potency.

Accordingly, the invention provides in one of its aspects a formulation comprising an epothilone, e.g. epothilone A or epothilone B, which hereinafter may be referred to as a formulation or formulations of the present invention.

In a preferred embodiment the invention provides a formulation in the form of an infusion concentrate which comprises an epothilone and a pharmaceutically acceptable organic solvent. The infusion concentrate does not require the use of a surfactant to improve the solubility of an epothilone, e.g. epothilone A and B, and/or render them more rapidly soluble. As stated above, surfactants such as a polyhydrogenated natural or hydrogenated castor oil, e.g. of an HLB value greater than 10, e.g. Cremophor®, may cause allergic reactions and they also can leach plasticisers from standard PVC containers, tubing and the like. Consequently, when they are employed one may be required to use special infusion apparatus, e.g. nitro-glycerine tubing and non-plasticised containers, such as glass, tubing and the like.

The aforementioned pharmaceutically acceptable organic solvent may be chosen from any such organic solvent known in the art. Said solvents may be used individually or as combinations with other solvents. Preferably the solvent is selected (i) from an alcohol with a carbon chain length of at least 2 or (ii) from an N-alkylpyrolidone, e.g. N-methylpyrolidone. Typical examples of alcohols are, e.g. a water miscible alcohol, e.g. absolute ethanol, or glycerol. Other alcohols include glycols, e.g. any glycol obtainable from an oxide such as ethylene oxide, e.g. propylene glycol. Other examples are polyols, e.g. a polyalkylene glycol, e.g. poly($C_{2-3}$)alkylene glycol. A typical example is a polyethylene glycol, e.g. of a preferred molecular weight of 200–600 daltons, more preferably, 200–400 daltons, especially 300. Polyethylene glycols may be used in distilled form and may be characterised for example by one or more of the following features: (i) an ethylene oxide content of maximally 20 ppm, typically less than 1 ppm, (ii) the absence of reducing substances and aldehydes (as determined by comparing the colour of a solution to a reference solution containing iron and cobalt chloride salts), (iii) a water content of less than 0.5% by weight, typically less than 0.1%, and (iv) a pH value between 4.0 to 7.0. For example a preferred glycol, e.g. polyethyleneglycol 300 may have an average molecular weight of 299, a pH value of 5.3, and may contain less than 1 ppm ethylene oxide, and less than 0.1% water. One skilled in the art would realize that polyethylene glycols of various molecular weights may be used as long as they are physiologically acceptable. The aforementioned solvents may contain occluded water. However, if desired, the pharmaceutically acceptable solvent may be mixed with water ("added water"), e.g about up to 45% water, e.g. up to 30%, e.g, 20%, e.g. 5%. Typical examples include ethanol/water mixtures, e.g 70% ethanol w/v, or polyethylene glycol/water mixtures, e.g. 90% polyethylene glycol w/v.

The epothilones, for example epothilone A or epothilone B, may be present in an infusion concentrate in a concentration of 0.1 to 100 mg/ml, e.g. 1 to 100 mg/ml, more preferably 0.5 to 50 mg/ml, more preferably 0.5 to 10 mg/ml, most preferably 1 mg/ml.

An epothilone, e.g. epothilone A or epothilone B, may be used individually or as a mixture of epothilones, e.g. a mixture of epothilone A and B. Given the stronger anti-tumour activity of epothilone B it may be employed in a lower concentration than epothilone A in the formulation. When used alone it is preferable to employ a concentration of epothilone A of 0.1 to 100 mg/ml, e.g. 10 to 100 mg/ml, preferably 0.1 to 50 mg/ml, e.g. 20 to 50 mg/ml, and especially 1 mg/ml. Epothilone B if used alone, is preferably employed in a concentration of 0.1 to 50 mg/ml, e.g. 10 to 50 mg/ml, e.g. 1 to 50 mg/ml, and especially 1 mg/ml.

Thus, in another aspect the present invention provides a pharmaceutical formulation, e.g. in the form of an infusion concentrate, comprising an epothilone, e.g. at a concentration of 0.1 to 100 mg/ml, preferably 0.5 to 50 mg/ml, more preferably 0.5 to 10 mg/ml, most preferably 1 to 5 mg/ml, and a pharmaceutically acceptable organic solvent, for example an alcohol, e.g. absolute ethanol or ethanol/water mixtures, e.g 70% ethanol, a polyol, e.g. propylene glycol, polypropylene glycol, polyethylene glycol 300, polyethylene glycol 400, aqueous polyethylene glycol solutions, e.g. 90% polyethylene glycol 300, or N-methylpyrolidone, more preferably polypropylene glycol or 70% ethanol, most preferably polyethylene glycol 300.

A formulation of the present invention in the form of an infusion concentrate may be produced by working up, e.g. dissolving, an epothilone in a pharmaceutically acceptable solvent of the invention, optionally with other excipients.

Infusion concentrates of the present invention are conveniently stored in suitable containers, e.g. vials, double-chamber vial systems, or ampoules. Typically the vials or ampoules are made from glass, e.g. borosilicate or soda-lime glass. The vials or ampoules may be of any volume conventional in the art, preferably they are of a size sufficient to accommodate 1 to 5 ml, more preferably 2 ml, of an infusion concentrate. The containers may accommodate preferably a stopper that can be pierced, e.g. a sterile rubber stopper, which may provide an appropriate hermetic seal with the container to allow for transfer of a liquid from or to the container.

The formulations of the present invention in the form of infusion concentrates may be stable for an extended period of time, e.g. up to 12 to 36, e.g. 24, months at temperatures of at least 2 to 8° C., as indicated in standard stability tests, e.g. as described in the examples.

Furthermore, the infusion concentrates exhibit little evaporation, they may be produced using conventional equipment, e.g. no explosion-proof equipment is necessary, and they can tolerate rubber stoppers when stored in containers, e.g. without causing the stoppers to degrade.

Infusion concentrates may be diluted in an aqueous medium suitable for intravenous administration to form an infusion solution, before the epothilone is administered parenterally, e.g. intravenously, to a patient. It is understood that, parenteral administration includes administration by infusion or injection.

Accordingly, the invention provides in another of its aspects an infusion solution comprising in admixture an infusion concentrate as hereinabove defined and a diluent selected from a pharmaceutically acceptable solvent, which is preferably an aqueous medium.

The pharmaceutically acceptable solvent used as a diluent may be any of those solvents or combinations of solvents used in the infusion concentrate. Preferably however it consists of water, i.e. water-for-injection. The infusion solution preferably has the same or essentially the same osmotic pressure as body fluid. Accordingly, the diluent, e.g. preferably contains an isotonic agent or agents which has the effect of rendering the osmotic pressure of the infusion solution the same or essentially the same as body fluid.

The isotonic agent or agents may be selected from any of those known in the art, e.g. mannitol, dextrose, glucose and sodium chloride. Preferably the isotonic agent is glucose or sodium chloride. The isotonic agent or agents may be used in amounts which impart to the infusion solution the same or essentially the same osmotic pressure as body fluid. The precise quantities needed can be determined by routine experimentation and may depend upon the composition of the infusion solution and the nature of the isotonic agent or agents. Selection of a particular isotonic agent or agents may be made having regard to the properties of the epothilone, e.g. epothilone A or epothilone B. For example, when epothilone B is employed alone or in combination with epothilone A, the use of certain isotonic agent or agents may cause the infusion solution to turn turbid. The turbidity may be attributed to the dissolution of the epothilone, e.g. epothilone B.

Surprisingly, we have found that if one employs glucose as the isotonic agent then the turbidity does not appear for long periods, e.g exceeding 24 hours, if at all.

The concentration of isotonic agent or agents in the aqueous medium will depend upon the nature of the particular isotonic agent or agents used. When glucose is used it is preferably used in a concentration of from 1 to 5% weight/volume (w/v), more particularly 5% w/v. When the isotonic agent is sodium chloride it is preferably employed in amounts of up to 1% w/v, in particular 0.9% w/v.

Infusion solutions according to the invention may comprise other excipients commonly employed in formulations to be administered intravenously. Excipients include antioxidants. Antioxidants may be employed to protect the epothilone, e.g. epothilone B, against oxidative degradation. Antioxidants may be chosen from any of those antioxidants known in the art and suitable for intravenous formulations. The amount of antioxidant may be determined by routine experimentation. As an alternative to the addition of an antioxidant, or in addition thereto, the antioxidant effect may be achieved by displacing oxygen (air) from contact with the infusion solution. This may be conveniently carried out by purging the container holding said infusion solution with an inert gas, e.g. nitrogen.

The amount of diluent used in admixture with the infusion concentrate in order to form an infusion solution may be chosen according to the desired concentration of epothilone, e.g. epothilone B, in the infusion solution. Preferably the infusion solution is prepared by mixing a vial or ampoule of infusion concentrate aforementioned with a diluent, e.g. a 5% w/v glucose solution in water-for-injection in a suitable container, e.g. an infusion bag or bottle, making the volume up to between 50 ml and 1000 ml, e.g. 200 ml and 1000 ml or preferably 50 to 100 ml, with the diluent. The infusion solution so formed may be preferably used immediately or within a short time of being formed, e.g. within 6 hours. Alternatively, the infusion concentrate and a predetermined amount of diluent, may be loaded each into separate chambers of a double-chamber vial system and only mixed immediately prior to intravenous administration to a patient.

In an alternative embodiment a formulation of the present invention may be in the form of a lyophilised composition comprising an epothilone, e.g. epothilone A or epothilone B. Given the poor solubility of epothilone A and B a lyophilisate mass consisting only of an epothilone, e.g. epothilone A or epothilone B, may be very small such that it does not provide a lyophilised composition of suitable bulk to be handled conveniently or even to the extent that it may even be difficult to detect visually. Accordingly, one may use excipients in a lyophilised composition according to the invention which act to increase the solids content and therefore the bulk of the lyophilised composition. Suitable excipients may be any of those excipients which used alone or in combination will increase the bulk of the lyophilised composition without adversely interacting with the epothilone such as to destabilise the epothilone or otherwise reduce its potency. Additionally, the excipients need to be suitable for use in pharmaceutical formulations, e.g. parenteral formulations. Therefore when selecting an excipient or excipients consideration must be given not only to the nature of the lyophilised composition but also to the nature of the final pharmaceutical form. Examples of suitable excipients include sodium or potassium phosphates, citric acid, tartaric acid, gelatin, lactose and other carbohydrates such as dextrose, mannitol and dextran and any of the cyclodextrins which are suitable for use intravenously, e.g. a beta-cyclodextrin. Typical beta-cyclodextrins include also beta-cyclodextrin derivatives, e.g. alkyl-, allyl-, or hydroxyalkyl-derivatives. In a more preferred embodiment the beta-cyclodextrin derivative may be hydroxypropyl-beta-cyclodextrin. Preferably the hydroxypropyl-beta-cyclodextrin may be any of those mentioned by Roger A. Rajewski et al in the Journal of Pharmaceutical Sciences, Vol. 85, No. 11, November 1996, pages 1142 through 1169, which article is incorporated herein by reference.

Through judicious selection of excipients the applicant has found that a suitably bulky lyophilised composition comprising epothilone A or epothilone B may be formed which exhibits improved solubility characteristics of epothilone A or epothilone B or renders the epothilones more rapidly soluble but which does not adversely affect the potency of the epothilones.

The excipients or mixtures thereof may contribute to 50 to 99.9% of the total solids content of the lyophilisate, more preferably 90 to 99%, e.g. 95% of total solids of said composition. The epothilone may contribute 100% to the total solids content of the lyophilised composition although preferably it may contribute to 0.1 to 1.5%, e.g. 1.2% of total solids.

In another aspect the present invention provides a lyophilised composition comprising an epothilone, e.g. at a concentration of 0.1 to 100%, more preferably 0.1 to 10%, more preferably 0.1 to 1.5%, e.g. 1.2% of the total solids content of the lyophilised composition, and mannitol or a cyclodextrin, e.g. hydroxypropyl-beta-cyclodextrin.

To the extent that the epothilone and cyclodextrin or mannitol do not provide 100% of the total solids content of the lyophilised composition, the balance of solids may be provided by any excipients commonly used in the field of lyophilisates which are to be reconstituted for pharmaceutical use, e.g. any of the other excipients referred to hereinabove.

The moisture content of the lyophilised composition may be 3% or less of the total weight of the lyophilised composition.

Lyophilised compositions according to the invention are formed from solutions (hereinafter referred to as "original solutions") containing an epothilone, e.g. epothilone A or epothilone B, and suitable excipients as defined hereinabove. Suitable solvents for such original solutions are either water alone or aqueous based solvents containing pharmaceutically acceptable, water miscible organic solvents, e.g. alcohols, more particularly ethanol or polyethylene glycol.

Original solutions may contain from 0.01% to 0.5% (w/v) of epothilone, e.g. epothilone A or epothilone B.

Original solutions may be prepared by dissolving the epothilone, e.g. epothilone A or epothilone B, and excipients in a suitable solvent and thereafter filtering the solution through a filter, e.g. a sterile 0.22 micron filter. The original solution thus formed may be filled into vials of suitable volume, preferably having a volume of 30 ml and a fill volume of 4.2 ml.

In yet another aspect the present invention provides a method of producing a lyophilised composition which comprises the steps of (i) mixing an epothilone, e.g. epothilone A or epothilone B, with a pharmaceutically acceptable excipient, e.g. mannitol or a cyclodextrin, e.g. a hydroxypropyl-beta-cyclodextrin in a suitable solvent to form an original solution, and (ii) dehydrating the original solution.

Lyophilisation may be carried out according to known techniques. In a preferred process the aforementioned filled vials may be frozen in a lyophilisation chamber for approximately 3 hours at a temperature below the eutectic point, preferably approximately −40° C. Thereafter the lyophilisation chamber may be evacuated to about 0.1 to 0.2 millitorr. The temperature of the chamber may then be increased to effect sublimation of the frozen liquids. Preferably the temperature is increased to about 0° C. and this temperature may be maintained for a period of 8 to 15 hours to effect lyophilisation.

The lyophilised composition may be used in the production of parenteral formulations and so the lyophilisation process is preferably carried out under sterile conditions. Aseptic formation of solutions containing pharmaceutically active compounds, the aseptic filling of vials and lyophilisation processes under aseptic conditions are well known to the skilled addressee.

The dry lyophilised composition thus formed may contain up to about 3% moisture. Optionally however, a humidification step may be employed subsequent to lyophilisation wherein sterile water vapour may be introduced into the lyophilisation chamber at atmospheric pressure or at a reduced pressure as aforementioned. Of course, if the humidification step is carried out under reduced pressure, the pressure may vary with the introduction of the water vapour, and pressure changes can be monitored and pressure adjusted if necessary using techniques well known in the art. The humidification step may be completed with a time period of from 4 to 8 hours depending on whether it is carried out at atmospheric pressure or reduced pressure.

Lyophilised compositions obtained using a humidification step are hereinafter referred to as hydrated lyophilisates. Said hydrated lyophilisates may contain from 0.1 to 5% by weight of water.

Lyophilised compositions according to the present invention may be provided in single dosage container forms. The single dosage container forms may be of any suitable size. By "suitable size" is meant an appropriate size having regard to the volume of solution which will be needed to reconstitute the lyophilised composition. Any suitable containers may be used to provide these dosage forms. By "suitable" is meant any container which may be used in aseptic filling procedures and which is capable of maintaining a sterile environment and which is unreactive to the lyophilised composition. Preferred containers may be formed of glass, e.g. Type I glass and may have means to receive a stopper, e.g. a sterile rubber stopper which may cooperate with the walls of the container to provide a hermitic seal.

Preferred stoppers also may allow entry to the contents of the container for the purpose of introduction of a solvent, e.g. water for injection, for the lyophilised composition.

The lyophilised composition according to the invention may be storage stable for up to 24 months at a temperature of 2 to 30° C. Lyophilised compositions stored for these periods display no signs of degradation and the solubility characteristics remain unaffected.

When it is desired to provide a parenteral form of an epothilone, the lyophilised composition may be re-constituted, preferably just before administration.

Re-constitution may involve dissolving the lyophilised composition in water or some other pharmaceutically acceptable solvent as hereinabove described, for example physiological saline, an aqueous solution of a pharmaceutically acceptable alcohol, e.g. ethanol, propylene glycol, a polyethylene glycol, e.g. polyethylene glycol 300, and the like, or some other sterile injectable under aseptic conditions. The single dosage container form may be filled with an appropriate quantity of solvent having regard to the desired concentration of epothilone, e.g. epothilone A or epothilone B, required for parenteral administration. Such a reconstituted lyophilised composition may be preferably used immediately or within a short time of being formed, e.g. within 6 hours.

A formulation of the present invention in suitable form for parenteral administration, e.g. an infusion solution prepared by diluting an infusion concentrate or a reconstituted lyophilised composition, may be placed in containers chosen from any conventional container which is non-reactive to said formulations. Glass containers made from those glass types aforementioned are suitable although it is preferred to use plastics containers, e.g. plastics infusion bags.

Plastics containers may be principally those composed of thermoplastic polymers. Plastics materials may additionally comprise additives, e.g. plasticisers, fillers, antioxidants, antistatics and other additives conventional in the art.

Plastics suitable for the present invention should be resistant to elevated temperatures required for thermal sterilisation. Preferred plastics infusion bags are those made from PVC plastics materials known in the art.

A wide range of container sizes may be employed. When selecting a container size, consideration may be paid to the solubility of the epothilone in the particular solvent and the ease of handling and, if appropriate, storage of the container. It is preferred to use containers which can accommodate between about 200 to 1000 ml, e.g. 250 to 1000 ml, of infusion solution or reconstituted lyophilised composition.

A formulation of the present invention in suitable form for parenteral administration, e.g. an infusion solution prepared by diluting an infusion concentrate or a reconstituted lyophilised composition, may be preferably sterile. This may be readily accomplished, e.g. by filtration of said formulation through sterile filtration membranes. Aseptic formation of any composition in liquid form, the aseptic filling vials and/or combining of liquids for parenteral use with a suitable diluent under aseptic conditions are well known to the skilled addressee.

A formulation of the present invention in suitable form for parenteral administration, e.g. an infusion solution prepared by diluting an infusion concentrate or a reconstituted lyophilised composition, is useful for treatment and prevention of malignant proliferative disorders, for example the indications and conditions disclosed in WO 93/10121 and DE 41 38 042 A2, the contents of which are incorporated herein by reference. More specifically, they may be useful for the treatment of a tumour disease, e.g. a melanoma, ovarian cancer, pancreas cancer, neuroblastoma, head and neck cancer, bladder cancer, renal, brain, gastric or preferably a colorectal, prostate, breast, lung (especially non-small cell lung) or epidermoid, e.g. mouth, cancer, especially where these are refractory to treatment with other chemotherapeutics, especially of the taxane class of chemotherapeutics, such as TAXOL®, or 5-fluorouracil. Moreover, a formulation of the present invention in suitable form for parenteral administration, e.g. an infusion solution prepared by diluting an infusion concentrate or a reconstituted lyophilised composition, act in a similar fashion to intravenous solutions of the microtubule interacting agent Paclitaxel, and are beneficial in treating conditions for which Paclitaxel might be used. For certain tumours epothilones offer enhanced beneficial effects compared with Paclitaxel. For certain tumours, e.g. certain types of lung tumours, e.g. A549 lung epothilone B offers enhanced beneficial effects compared with Paclitaxel.

Generally, a formulation of the present invention in suitable form for parenteral administration, e.g. an infusion solution prepared by diluting an infusion concentrate or a reconstituted lyophilised composition, may be administered in an amount which is therapeutically effective against a proliferative disease that can be treated by administration of an epothilone, e.g. epothilone A and/or epothilone B, especially epothilone B. Such proliferative diseases include any proliferative disease as mentioned above, especially a tumour disease, the response to a therapeutically effective amount preferably manifesting itself in a diminished proliferation, e.g. diminished tumour growth or even (more preferably) tumor regression or (most preferably) tumour disappearance. The exact amount and the duration of administration may depend upon the nature of the epothilone, e.g. epothilone A, epothilone B or a mixture of both, the particular type of malignantly proliferating cells characteristic of the particular tumour, the seriousness of the condition, the rate of administration, as well as the patient's health and response to treatment.

Also, a formulation of the present invention in suitable form for parenteral administration, e.g. an infusion solution prepared by diluting an infusion concentrate or a reconstituted lyophilised composition, may be combined with other tumour treatments known to a skilled person, e.g. radiation, or administered as part of a combination therapy comprising at least one other chemotherapeutic agent. The administration of a combination of active agents may be simultaneous or consecutive, with either one of the active agents being administered first. The dosage of the active agents of a combination treatment may depend on effectiveness and site of action of each active agent as well as synergistic effects between the agents used for combination therapy.

Other chemotherapeutic agents may include especially any chemotherapeutic agent that is or can be used in the treatment of tumor diseases, such as chemotherapeutics derived from the following classes:

(A) Alkylating agents, preferably cross-linking chemotherapeutics, preferably bis-alkylating agents, (B) antitumour antibiotics, preferably doxorubicin (ADRIAMYCIN®, RUBEX®);

(C) antimetabolites;

(D) plant alkaloids;

(E) hormonal agents and antagonists;

(F) biological response modifiers, preferably lymphokines or interferons;

(G) inhibitors of protein tyrosine kinases and/or serine/threonine kinases;
(H) antisense oligonucleotides or oligonucleotide derivatives; or
(I) miscellaneous agents or agents with other or unknown mechanism of action, preferably of the Taxane class, especially Taxotere® or most especially paclitaxel (Taxol®).

A formulation of the present invention in suitable form for parenteral administration, e.g. an infusion solution prepared by diluting an infusion concentrate or a reconstituted lyophilised composition, may, therefore, be useful as single anti-cancer formulations or as part of a combination regimen for the treatment of various tumours.

The utility of all formulations of the present invention in suitable form for parenteral administration, e.g. an infusion solution prepared by diluting an infusion concentrate or a reconstituted lyophilised composition, may be observed in standard clinical trials in, for example, known indications of active agent dosages giving equivalent blood levels of active agent; for example using dosages in the range of about 0.1 to 6 mg/m$^2$ of active agent for weekly treatment and about 0.3 to 18 mg/m$^2$ of epothilone for three-weekly treatment for a 75 kilogram mammal, e.g. an adult human of 1.73 m2, and in standard animal models. For example, the anti-tumor effect of single dose regimens are investigated in a model of human ovarian cancer SKOV3 as well as a U373 glioma model.

The increased bioavailability of an epothilone administered in the form of (i) an infusion solution prepared by diluting an infusion concentrate or (ii) a reconstituted lyophilised composition infusion solution according to the present invention, may be observed in standard animal tests and in clinical trials, e.g. as described above and in detail in the examples. Naturally, the exact amounts of epothilone and of the formulation to be administered may depend on a number of factors, e.g. the condition to be treated, the desired duration of treatment and the rate of release of active agent. For example, the amount of epothilone required and the release rate thereof may be determined on the basis of known in vivo and in vitro techniques, for example as described above, determining how long a particular active agent concentration in the blood plasma remains at an acceptable level for a therapeutic effect.

Dosage forms may be conveniently administered intravenously in a dosage of from about 0.2 to 100 mg/m$^2$ epothilone A and from about 0.2 to 50 mg/m$^2$ of epothilone B. Preferably, for weekly treatment the dose is between 0.1 and 6, preferably 0.1 and 5 mg/m2, more preferably 0.1 and 3 mg/m2, even more preferably 0.1 and 1.7, most preferably 0.1 and 1 mg/m2; for three-weekly treatment the dose is between 0.3 and 18 mg/m2, preferably 0.3 and 15, more preferably 0.3 and 12, even more preferably 0.3 and 7.5 mg/m2, most preferably 1.0 and 3.0 mg/m2. This dosis is preferably administered to the human by intravenous (i.v.) administration during 2 to 180 min, preferably 2 to 120 min, more preferably during 5 to 30 min, most preferably during 10 to 30 min, e.g. during 30 min.

Preferably the concentration and dosage strength may be such to achieve an effective dose level of about 0.5 to 15 mg/day, more preferably 1 to 10 mg/day, more preferably 2 to 8 mg/day. The dose received by intravenous administration and the blood concentration may be determined accurately on the basis of known in vivo and in vitro techniques.

In yet another aspect the invention provides a method of administering an epothilone which comprises (a) diluting a pharmaceutical formulation according to the invention, e.g. in the form of an infusion concentrate or a lyophilised composition, with an aqueous medium, to form a solution suitable for parenteral, e.g. intravenous, administration, and (b) administering such a solution to the subject.

The invention is illustrated by way of the following examples which are not intended to limit the scope of the present invention.

EXAMPLES

Example 1

Epothilone (15 mg of B or 50 mg of A) is dissolved in 98–100% propylene glycol (1.0 ml). The solution is sterile filtered through a 0.22 microns pore size filter and charged to 1 ml ampoules. The filled ampoules are used for storage and shipment. The filled ampoules are stable for a period of at least 12 months at a temperature of 2 to 8° C. Prior to intravenous administration, the contents of an ampoule are added to 250 to 1000 ml of a 5% glucose solution in water-for-injection. The intravenous solution thus formed is stable for a period of 8 hours at room temperature.

Examples 2 to 7

The experiment of Example 1 is repeated using the absolute and aqueous ethanol solvent systems and various polyethylene glycol solvent systems (Table 1). Polyethylene glycols are used in distilled form are characterised for example by (i) an ethylene oxide content of maximally 20 ppm, typically less than 1 ppm, (ii) the absence of reducing substances and aldehydes (as determined by comparing the color of a solution to a reference solution containing iron and cobalt chloride salts), (iii) a water content of less than 0.5%, typically less than 0.1%, and (iv) a pH value between 4.0 to 7.0. For example polyethyleneglycol 300 has an average molecular weight of 299, a pH value of 5.3, and contains less than 1 ppm ethylene oxide, and less than 0.1% water.

TABLE 1

| Example | Solvent system |
|---------|----------------|
| 2 | Absolute ethanol |
| 3 | Polyethylene glycol 300 |
| 4 | Polyethylene glycol 400 |
| 5 | 50 to 100% ethanol (50 to 0% water) |
| 6 | Polyethylene glycol 300 90 to 100% (10 to 0% water) |
| 7 | Polyethylene glycol 400 90 to 100% (10 to 0% water) |

The infusion solutions obtained from Examples 2 to 7 are all stable for a period of 8 hours at room temperature.

Example 8

Solubilities in various solvent systems are summarized in Table 2. If not indicated otherwise all solubility data refer to T=22° C.

TABLE 2

Solubility of epothilone B in various solvent systems.

| Solvent/Solvent-system | Solubility [g/l] ± 10% |
|------------------------|------------------------|
| H$_2$O (pH 6.0) | 0.16 (0.19, 4° C.) |
| Phosphate buffer pH 7.4 | 0.16 (0.19, 4° C.) |
| H$_2$O, 0.9% glucose | 0.16 |
| H$_2$O, 5% glucose | 0.16 |

TABLE 2-continued

Solubility of epothilone B in various solvent systems.

| Solvent/Solvent-system | | Solubility [g/l] ± 10% |
|---|---|---|
| H₂O, 15% glycerin | | 0.19 |
| H₂O, 5% poloxamer 188 | | 0.23 |
| EtOH/H₂O (v/v) | 100/0 | >50 |
| | 50/50 | 27 |
| | 30/70 | 4.1 |
| | 20/80 | 1.3 |
| | 10/90 | 1.1 |
| PEG 300/H₂O (v/v) | 100/0 | 12 |
| | 50/50 | 10 |
| | 70/30 | 2.5 |
| | 30/70 | 0.9 |
| PEG 400/H₂O | 100/0 | 30 |
| (v/v) | 50/50 | 11 |
| | 70/30 | 2.3 |
| | 30/70 | 0.8 |
| Propylene glycol/H₂O | 100/0 | 26 |
| (v/v) | 70/30 | 10.4 |
| | 50/50 | 1.6 |
| | 30/70 | 0.6 |

The solubility of epothilone B in water at neutral pH is about 160 mg/l, and significantly higher solubility is achieved in PEG/water, propyleneglycol/water, or EtOH/water mixtures. In comparison, previously reported aqueous solubility of epothilone A is 940 mg/l and 700 mg/l for mixtures of epothilones A and B.

Example 9

The stability of aqueous versus nonaqueous polyethyleneglycol infusion concentrates comprising epothilone B at different concentration and various temperatures is determined. Typically, a known amount of epothilone B is dissolved in 1.0 ml of each of the various solvent systems and each solution is sterile filtered and charged to 1 ml white-glass vials with grey rubber stoppers and grey flip-off caps. Table 3 describes the amount of degradation product formed over a period of up to seven months. The stability is analyzed by determining formation of degradation products in each of the infusion concentrates as a function of time and temperature. Each sample is analyzed by HPLC, the sample is prepared by diluting the concentrate with an aqueous medium. The stability of all infusion concentrates after 3 months at 2 to 8° C. is comparable. At higher temperatures, e.g. 25° C., nonaqueous solvent systems comprising PEG exhibit generally higher stability than aqueous solvent systems comprising PEG.

TABLE 3

Proportion of degradation products in aqueous vs. nonaqueous PEG-containing infusion concentrates.

| Solvent system | Dosage | Time | 2–8° C. | 25° C. |
|---|---|---|---|---|
| PEG 400 | 1 mg/ml | 3 months | <0.1 | 0.2 |
| PEG 400/water 90:10 (w/w) | 1 mg/ml | 3 months | <0.1 | 0.4 |
| PEG 300 | 1 mg/ml | 3 months | <0.1 | — |
| PEG 300/water 90:10 (w/w) | 15 mg/ml | 7 months | <0.1 | 1.0 |
| ethanol/water 59:41 (w/w) | 5 mg/ml | initial | <0.1 | — |
| | | 1 month | 0.3 | |
| | | 5 months | 0.3 | |

Example 10

An aqueous solution is prepared by dissolving epothilone B (5.0 mg) and mannitol (1500 mg) in water for injection to make up a 30 ml solution. The solution is passed through a sterile 0.22 micron pore size membrane filter before aseptically filling the solution into a glass vial and thereafter aseptically fitting a sterile stopper to the vial in readiness for the drying process. The filled vial is then positioned in a lyophilisation chamber and cooled to a temperature of about −40° C. The lyophilisator condenser is cooled to about −60° C. and the chamber is evacuated to about 0.1 milltorr. The chamber temperature is set to about 20° C. to start the drying process. After about 20 hours of drying the chamber pressure has increased to about 0.2 millitorr and the drying process is deemed complete. The pressure of the chamber is increased to atmospheric pressure by aseptically introducing sterile air or nitrogen into the chamber. Thereafter the stopper is aseptically seated onto the vial to provide a hermitic sterile seal. The sealed vial provides a single dose container of epothilone B which is reconstituted shortly before administration with 25 ml of water for injection. The dosage is administered intravenously. The lyophilised product possesses the desired characteristics required of the lyophilised compositions according to the invention.

Examples 11 to 14

The methodology of Example 10 is carried out in respect of the tabulated components set forth hereinbelow to form lyophilised products (Table 4).

TABLE 4

| Example | Epothilone B mg | hydroxypropyl-beta cyclodextrin/mg | Water for Injection/ml |
|---|---|---|---|
| 11 | 5.0 | 400 | up to 4.2 |
| 12 | 5.0 | 500 | up to 5.0 |
| 13 | 5.0 | 420 | up to 4.2 |
| 14 | 5.0 | 420 | up to 8.5 |

The lyophilised products formed according to Examples 11 to 14 possess the desired characteristics required of the lyophilised compositions according to the invention.

What is claimed is:

1. A pharmaceutical formulation in the form of an infusion concentrate for treating a proliferative disease sensitive to an epothilone comprising the epothilone dissolved in a pharmaceutically acceptable organic solvent selected from the group consisting of ethanol, a mixture of ethanol and water, wherein the volume to volume ratio of ethanol to water ratio is in the range from almost about 100:0 to about 10:90, propylene glycol, propylene glycol 300, polyethylene glycol 400, and a mixture of propylene glycol, polyethylene glycol 300 or polyethylene glycol 400 with water, wherein the volume to volume ratio of propylene glycol, polyethylene glycol 300 or polyethylene glycol 400 to water is in the range from about 100:0 to almost about 30:70.

2. A pharmaceutical formulation according to claim 1 comprising an epothilone and a pharmaceutically acceptable organic solvent in the absence of a surfactant having an HLB value of 10 or above.

3. A pharmaceutical formulation according to claim 1 wherein the pharmaceutically acceptable organic solvent is a polyethylene glycol.

4. A pharmaceutical formulation according to claim 1 comprising epothilone B and polyethylene glycol 300.

5. A pharmaceutical formulation according to claim 1 wherein water is present in an amount of up to 45% w/v.

6. A pharmaceutical formulation according to claim 1 wherein water is present in an amount of up to 0.5% w/v.

7. A pharmaceutical formulation according to claim 1 wherein the epothilone is at a concentration of 1 to 5 mg/ml.

8. An infusion solution obtained by diluting an infusion concentrate according to claim 1 with a pharmaceutically acceptable solvent.

9. An infusion solution of claim 8 wherein the pharmaceutically acceptable solvent is an aqueous medium.

10. A pharmaceutical formulation of claim 1 comprising the epothilone at a concentration of from 0.1 to 100 mg/ml in the absence of a surfactant having an HLB value of 10 or above.

11. The pharmaceutical formulation of claim 1 wherein the epothilone is epothilone B which is present in a concentration of from 0.1 to 100 mg/ml.

12. A pharmaceutical formulation of claim 11 wherein the epothilone is epothilone B and the concentration is in the range from 1 to 5 mg/ml.

13. An infusion solution obtained by diluting an infusion concentrate according to claim 12 with a pharmaceutically acceptable solvent.

14. A pharmaceutical formulation of claim 1 wherein the epothilone is epothilone B and its concentration is in the range from 0.1 to 50 mg/ml.

15. A pharmaceutical formulation of claim 14 which does not contain a polyoxyethylene castor oil derivative having an HLB value of 10 or above.

16. A pharmaceutical formulation of claim 1 wherein the organic solvent is polyethylene glycol 300 or polyethylene glycol 400 and the epothilone is epothilone B.

17. A pharmaceutical formulation of claim 16 wherein the concentration of epothilone B is in the range from 1 to 5 mg/ml.

18. An infusion solution obtained by diluting an infusion concentrate according to claim 17 with a pharmaceutically acceptable solvent.

19. A method of administering an epothilone for the treatment of a proliferative disease sensitive to treatment with an epothilone to a mammal in need of such treatment in a therapeutically effective amount which comprises:
   (a) diluting a pharmaceutical formulation according to claim 1 with an aqueous medium to form an infusion solution and
   (b) administering the infusion solution intravenously to the subject.

20. A method of claim 19 wherein the infusion solution is administered over a period of from 2 minutes to 180 minutes.

* * * * *

UNITED STATES PATENT AND TRADEMARK OFFICE
CERTIFICATE OF CORRECTION

PATENT NO. : 6,683,100 B2
DATED : January 27, 2004
INVENTOR(S) : Peter van Hoogevest It is certified that error appears in the above-identified patent and that said Letters Patent is hereby corrected as shown below:

Column 12,
Line 44, claim 1 should read as follows:

-- 1. A pharmaceutical formulation in the form of an infusion concentrate for treating a proliferative disease sensitive to an epothilone comprising the epothilone dissolved in a pharmaceutically acceptable organic solvent selected from the group consisting of ethanol, a mixture of ethanol and water, wherein the volume to volume ratio of ethanol to water ratio is in the range from almost about 100:0 to about 10:90, propylene glycol, polyethylene glycol 300, polyethylene glycol 400, and a mixture of propylene glycol, polyethylene glycol 300 or polyethylene glycol 400 with water, wherein the volume to volume ratio of propylene glycol, polyethylene glycol 300 or polyethylene glycol 400 to water is in the range from about 100:0 to almost about 30:70. --

Signed and Sealed this

Eighth Day of February, 2005

JON W. DUDAS
*Director of the United States Patent and Trademark Office*